(12) United States Patent
Chang et al.

(10) Patent No.: US 7,684,042 B2
(45) Date of Patent: Mar. 23, 2010

(54) DEVICE HAVING AN OPTICAL PART FOR ANALYZING MICRO PARTICLES

(75) Inventors: Jun Keun Chang, Seoul (KR); Alexey Dan Chin-Yu, Seoul (KR); Jung Kyung Kim, Seoul (KR); Chanil Chung, Kyunggi-Do (KR); Sun Hee Lim, Seoul (KR)

(73) Assignees: Digital Bio Technology, Seoul (KR); Seoul National University Industry Foundation, Seoul (KR)

( * ) Notice: Subject to any disclaimer, the term of this patent is extended or adjusted under 35 U.S.C. 154(b) by 581 days.

(21) Appl. No.: 11/547,479

(22) PCT Filed: Nov. 3, 2004

(86) PCT No.: PCT/KR2004/002814

§ 371 (c)(1),
(2), (4) Date: Oct. 2, 2006

(87) PCT Pub. No.: WO2005/095925

PCT Pub. Date: Oct. 13, 2005

(65) Prior Publication Data

US 2008/0278726 A1    Nov. 13, 2008

(30) Foreign Application Priority Data

Mar. 31, 2004    (KR)  ............... 10-2004-0022331

(51) Int. Cl.
    *G01N 21/25* (2006.01)
(52) U.S. Cl. ................................. 356/417
(58) Field of Classification Search ............... 356/300, 356/303, 338, 417–418; 359/867
    See application file for complete search history.

(56) References Cited

U.S. PATENT DOCUMENTS

| 4,954,722 | A | 9/1990 | Fine et al. |
| 5,089,714 | A | 2/1992 | Ludlow et al. |
| 5,471,299 | A | 11/1995 | Kaye et al. |
| 5,484,571 | A * | 1/1996 | Pentoney et al. ......... 422/82.08 |
| 6,259,713 | B1 * | 7/2001 | Hwu et al. ................. 372/36 |

FOREIGN PATENT DOCUMENTS

| JP | 7-37937 | 4/1995 |
| JP | 2002-131214 | 5/2002 |

* cited by examiner

*Primary Examiner*—Tarifur Chowdhury
*Assistant Examiner*—Abdullahi Nur
(74) *Attorney, Agent, or Firm*—Browdy and Neimark, PLLC

(57) ABSTRACT

Disclosed is a micro particle analyzing device illuminating light to fluid including micro particles, reading the lights emitted from the micro particles at a signal processing reading section and thus analyzing the micro particles. The device comprises a light source section emitting light which will be illuminated to the fluid; a lens regulating an amount and a focal distance of the light emitted from the light source; and a concave mirror condensing light emitted from the micro particle to reflect it to the reading section wherein the concave mirror is formed with a hole so that the light of the light source section having passed through the lens can pass through the concave mirror. When analyzing the micro particles using the analyzing device according to the invention, the amounts of lights emitted from the micro particles according to up-and-down positions of the micro particles are not different.

16 Claims, 15 Drawing Sheets

-PRIOR ART-

DEVICE HAVING AN OPTICAL PART FOR ANALYZING MICRO PARTICLES

TECHNICAL FIELD

The present invention relates to a micro particle analyzing device illuminating light to fluid including micro particles and reading light emitted from the micro particle at a signal processing reading section and thus analyzing the micro particles. The micro particle analyzing device comprises a light source section emitting light which will be illuminated to the fluid; a lens regulating an amount and a focal distance of the light emitted from the light source and having a small numerical aperture; and a concave mirror condensing light emitted from the micro particle to reflect it to the reading section and having a large numerical aperture. A hole is formed in the concave mirror so that the light of the light source section having passed through the lens can pass through the concave mirror.

BACKGROUND ART

A micro particle analyzing device according to the prior art, for example, a flow cytometry analyzing a blood cell such as erythrocyte or leukocyte in blood uses a flow cell having a rectangular cross section and makes a sample solution, which includes micro particles to be analyzed, flow to a central part thereof. FIG. 1 shows an optical part for analyzing the sample flowing in the flow cell having the rectangular cross section. This structure has a characteristic of transverse illumination. That is, an incident path of a laser light source intersects an emission path of fluorescence generated by a micro particle excited due to the illumination from the light source.

The transverse illumination device for analyzing micro particles comprises a light source section 10 emitting light which will be illuminated to a sample; a cylindrical lens 20 regulating an amount and a focal distance of the light emitted from the light source 10; an object lens 40 adjacent to the sample to condense light emitted from the sample; a reflecting mirror 50 for reflecting the light having passed through the object lens to a reading section 80; and a reading section 80 sensing and reading the light emitted from the sample.

To analyze the erythrocyte or leukocyte in fluid, fluid is made to flow in a flow cell 90 mounted to the micro particle analyzing device.

FIG. 2 shows a cross section of the flow cell. The fluid flows to a sample injecting inlet 91, and a buffer solution 94 is injected to a buffer solution injecting inlet 92 to flow around the sample. The sample responds to light of the light source 10 and emits light when passing through an observation point 93.

Preferably, the flow cell 90 or the sample is treated with fluorescent material in advance. When the micro particle (for example, erythrocyte) in the sample is illuminated with light of the light source 10, it responds the light together with the fluorescent material and emits light having a specific wavelength band. The light is selectively passed through a filter 70 and then can be signal-processed at a signal processing reading section 80 (for example, photo multiplier tube (PMT) or CCD camera).

The above micro particle analyzing device may further comprise an aperture 60 and the filter 70 so that only light having a specific wavelength band of the emission lights can be passed through.

In recent years, a microchip based flow cytometry using a microchip including a micro channel as a flow cell to analyze a micro amount of sample has been researched and developed. When using a microchip 540 as shown in FIG. 6, since the microchip has a flat horizontal structure, it is adopted an optical structure such that laser light is incident through an object lens and fluorescence emitted from a micro particle is focused at the same time (i.e., axial illumination).

The transverse illumination shown in FIG. 1 can mount different standards of optical devices at the incident path of the light source and the emission path of the fluorescence. However, in the axial illumination as shown in FIGS. 3 and 4, characteristics of the incident light and the emission fluorescence are determined depending on the standard of the object lens.

The above characteristic of the axial illumination causes a disadvantage that it is impossible to independently regulate a light spot form of an incident light and a focused form of emission fluorescence each other.

To secure a uniformity of scattered light or fluorescence signal emitted from a sample particle in the microchip based flow cytometry, a magnitude of the light spot of the incident laser light should be large enough to include the sample particle. In addition, it should emit regular lights without regard to upper and lower positions of the particles to the light spot. Accordingly, it is preferred to use a lens having a small numerical aperture. However, when the emission light of the micro particle is again focused with the lens having the small numerical aperture, there is a problem of decreasing a focusing efficiency of emission light. The reason is because a lens having a large numerical aperture is preferred to focus the emission light of the micro particle.

Accordingly, ideal conditions of the optical part applied to the flow cytometry are as follows. An incident light is made to pass through a lens having a small numerical aperture and then to illuminate the sample particle. An emission light is made to pass through a lens having a large numerical aperture and then to be detected at a sensing section.

DISCLOSURE OF INVENTION

Accordingly, the present invention has been made to solve the above-mentioned problems occurring in the prior art. The object of the present invention is to provide a micro particle analyzing device comprising a concave mirror for condensing light emitted from the micro particle and reflecting it to a reading section and having a hole formed therein through which light having passed through a lens can pass. When analyzing the micro particle using the analyzing device, amounts of the lights emitted from the micro particles become not different according to upper and lower positions of the micro particles.

Like this, the object of the invention is to provide a micro particle analyzing device comprising a concave mirror having a large numerical aperture and a hole formed therein through which light of a light source section having passed through a lens having a small numerical aperture can pass.

In addition, another object of the invention is to provide a concave mirror used for the micro particle analyzing device and having a structure as described above.

In order to accomplish the object, there is provided a micro particle analyzing device illuminating light to fluid including micro particles, reading the lights emitted from the micro particles at a signal processing reading section and thus analyzing the micro particles. The micro particle analyzing device comprises a light source section emitting light which will be illuminated to the fluid; a lens regulating an amount and a focal distance of the light emitted from the light source and having a small numerical aperture; and a concave mirror condensing light emitted from the micro particle to reflect it to the reading section and having a large numerical aperture. A hole is formed in the concave mirror so that the light of the light source section having passed through the lens can pass through the concave mirror.

According to the invention, since the lens is provided to regulate, an amount and a focal distance of light of light source section and to illuminate the light to the fluid, a numerical aperture of the lens is preferably small. For example, it is preferred to use a convex lens having a numerical aperture of about 0.1 or less. A numerical aperture of a lens used in the following embodiment is about 0.01.

According to the invention, since the concave mirror is provided to condense the light emitted from the micro particle and to reflect it to the signal processing reading section, a numerical aperture of the concave mirror is preferably large. For example, it is preferred to use a concave mirror having a numerical aperture of about 0.1 or more. A numerical aperture of a concave mirror used in the following embodiment is about 0.5.

In addition, the concave mirror is preferably a parabolic mirror. In particular, the concave mirror is a hemiparabolic mirror which is a part of a parabolic mirror, as described in the following embodiment.

According to an embodiment of the invention, the hole formed in the concave mirror may be situated at a place deviated from a central axis of the parabolic mirror. The hole has a diameter suitable for the pass of the light having passed through the lens. When the hole is formed like this, the amount of emission lights which are lost when passing through the hole is also negligibly small when condensing and transmitting the light emitted from the micro particle to the signal processing reading section. For example, when the hole is made to have a diameter of about 1 to 2 mm as an embodiment which will be hereinafter described, the light can pass through the concave mirror and it is possible to neglect the amount of emission lights of the micro particles which are lost when passing through the hole. The diameter of the hole can be properly changed depending on light sources used.

In addition, the micro particle analyzing device according to the invention can be used as a device illuminating light to fluid flowing in a channel provided in a microchip made of plastics and analyzing the fluid. At this time, left and right wall surfaces of the micro channel is preferably asymmetrical so that the micro particle is focused to pass through only a predetermined region of the micro channel. In other words, preferably, the micro channel comprises a nozzle part formed by left and right walls having slanted surfaces, a cross section of the nozzle part in a width direction is reduced from an inlet of the nozzle part to an outlet of the nozzle part, and a longitudinal sectional shape of the micro channel is right and left asymmetrical on the basis of a central line of the micro channel in the longitudinal direction thereof. In particular, the slanted surface of any one of the left and right walls constructing the nozzle part is preferably more close to the inlet of the micro channel than the slanted surface of the other wall is.

Accordingly, when the fluid including the micro particles is focused, it is possible to prevent the micro particles from combining with each other and thus blocking the micro channel (i.e., bottleneck phenomenon).

According to another embodiment of the invention, there is provided a concave mirror used for the micro particle analyzing device. The concave mirror is optically combined with a lens having a small numerical aperture and regulating an amount and a focal distance of light emitted from a light source so that the light is illuminated to a sample, and has a large numerical aperture for condensing light emitted from the sample and reflecting it to a signal processing reading section and a hole formed therein so that the light of the light source having passed through the lens can pass through the concave mirror.

Preferably, the concave mirror is a hemiparabolic mirror having a numerical aperture of 0.1 or more and optically combined with a lens having a numerical aperture of 0.1 or less.

The concave mirror may be manufactured according to a typical manufacturing method of an optical mechanism.

BRIEF DESCRIPTION OF DRAWINGS

The above and other objects, features and advantages of the present invention will be more apparent from the following detailed description taken in conjunction with the accompanying drawings, in which:

FIG. 14 shows real detected signals of micro particles detected at signal process reading sections of an axial illumination device for analyzing micro particles according to the prior art and a micro particle analyzing device according to an embodiment of the invention, respectively.

Figure 1:
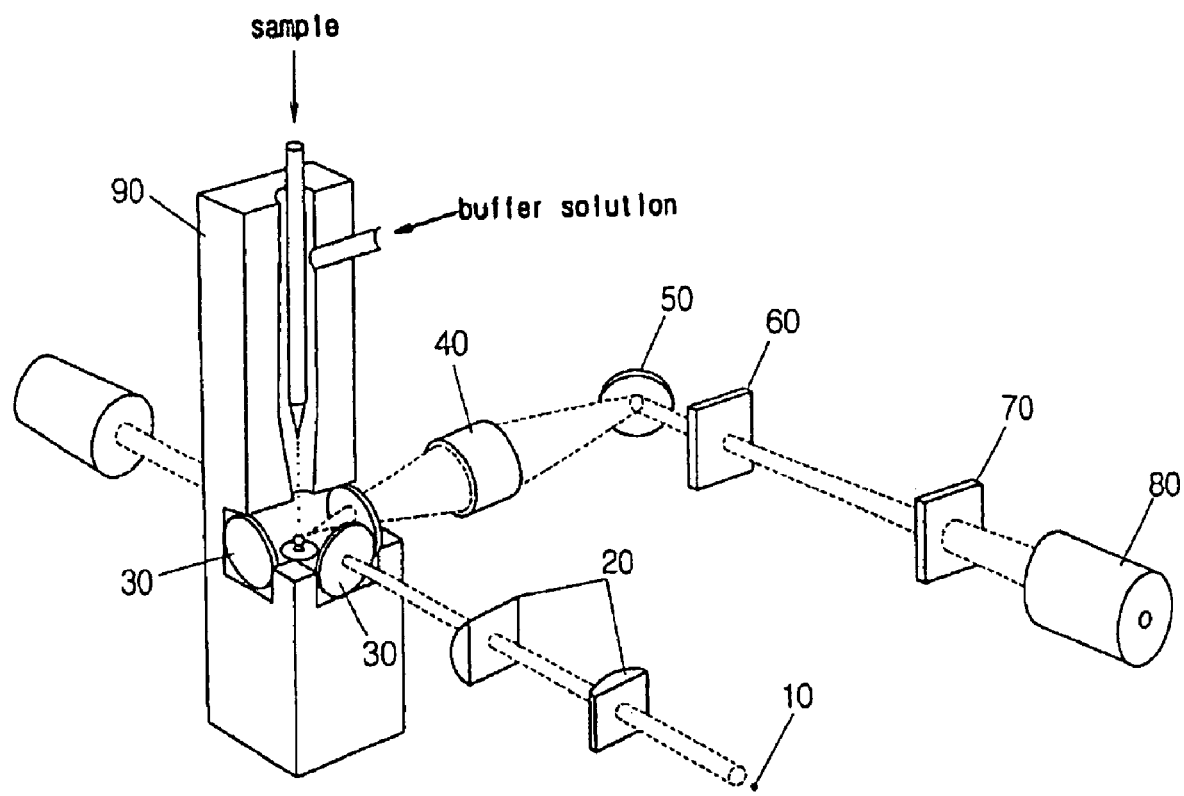
FIG. 1 is a structural view showing a transverse illumination device for analyzing micro particles according to the prior art.
Figure 2:
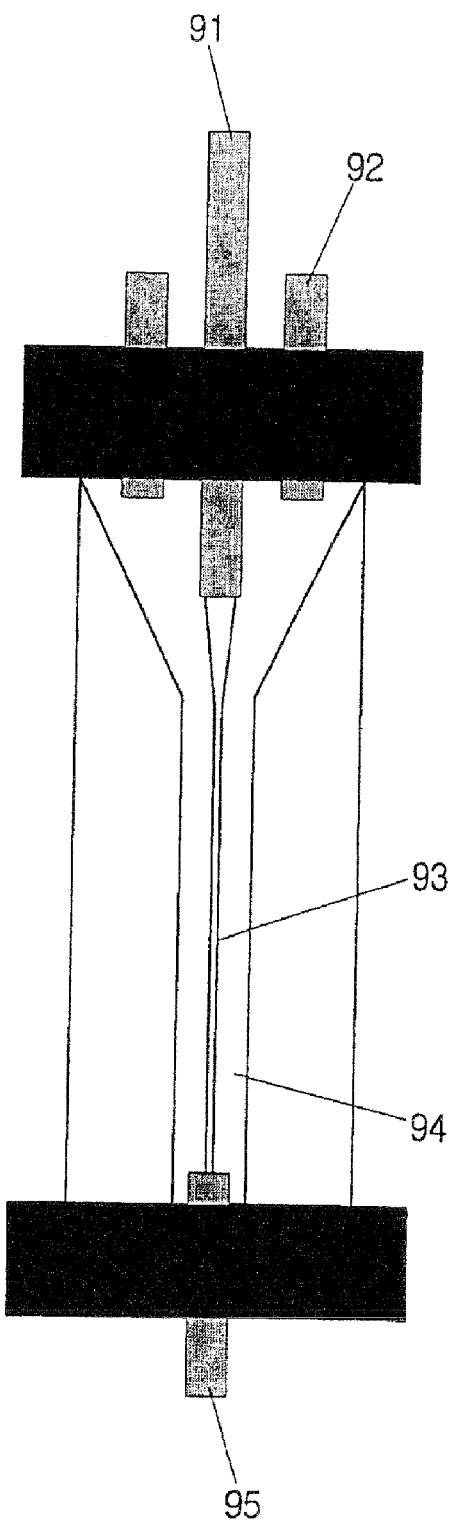
FIG. 2 is a sectional view illustrating a flow cell of the analyzing device shown in FIG. 1 in which a sample flows.
Figure 3:
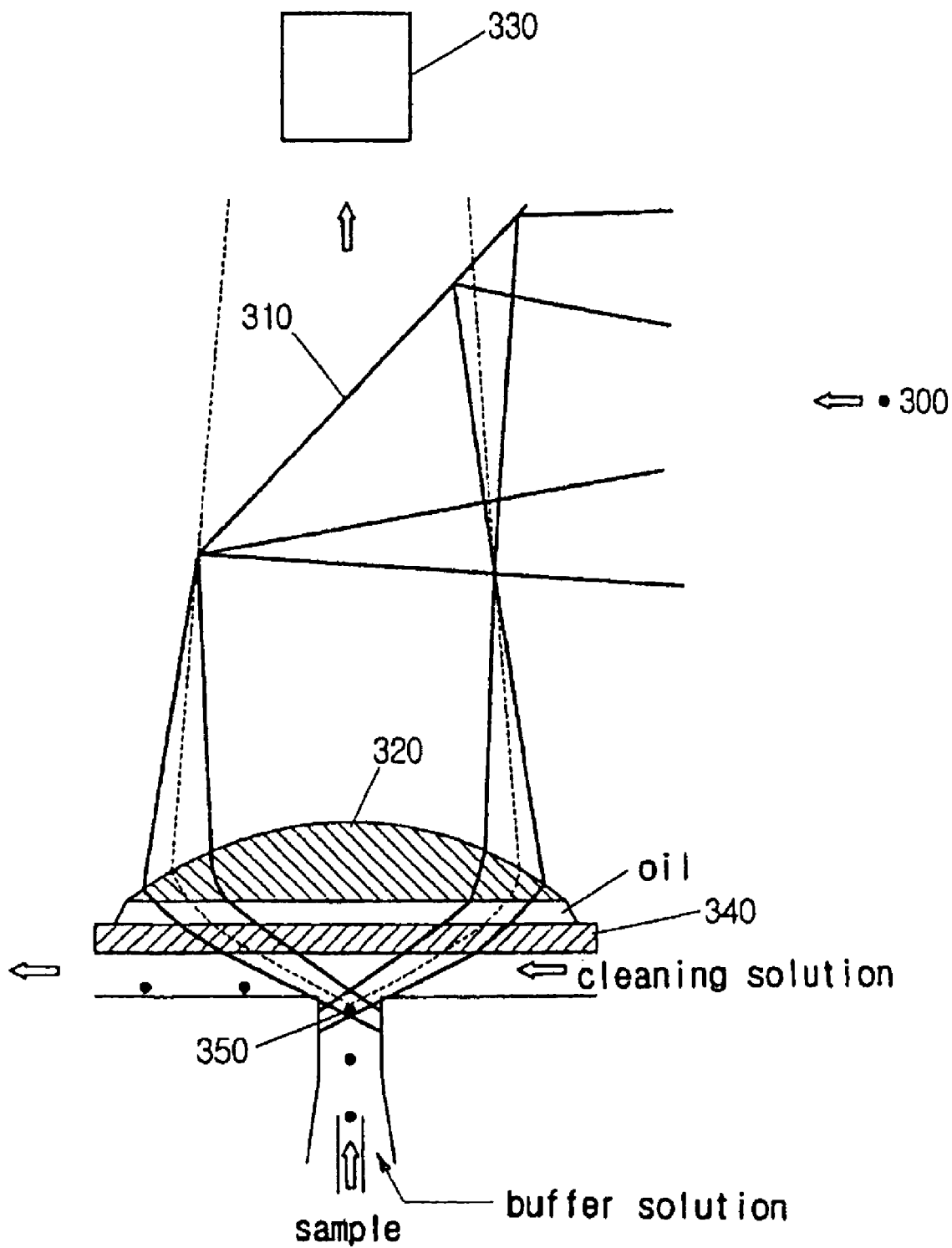
FIG. 3 is a sectional view of an axial illumination device for analyzing micro particles according to the prior art.
Figure 4:
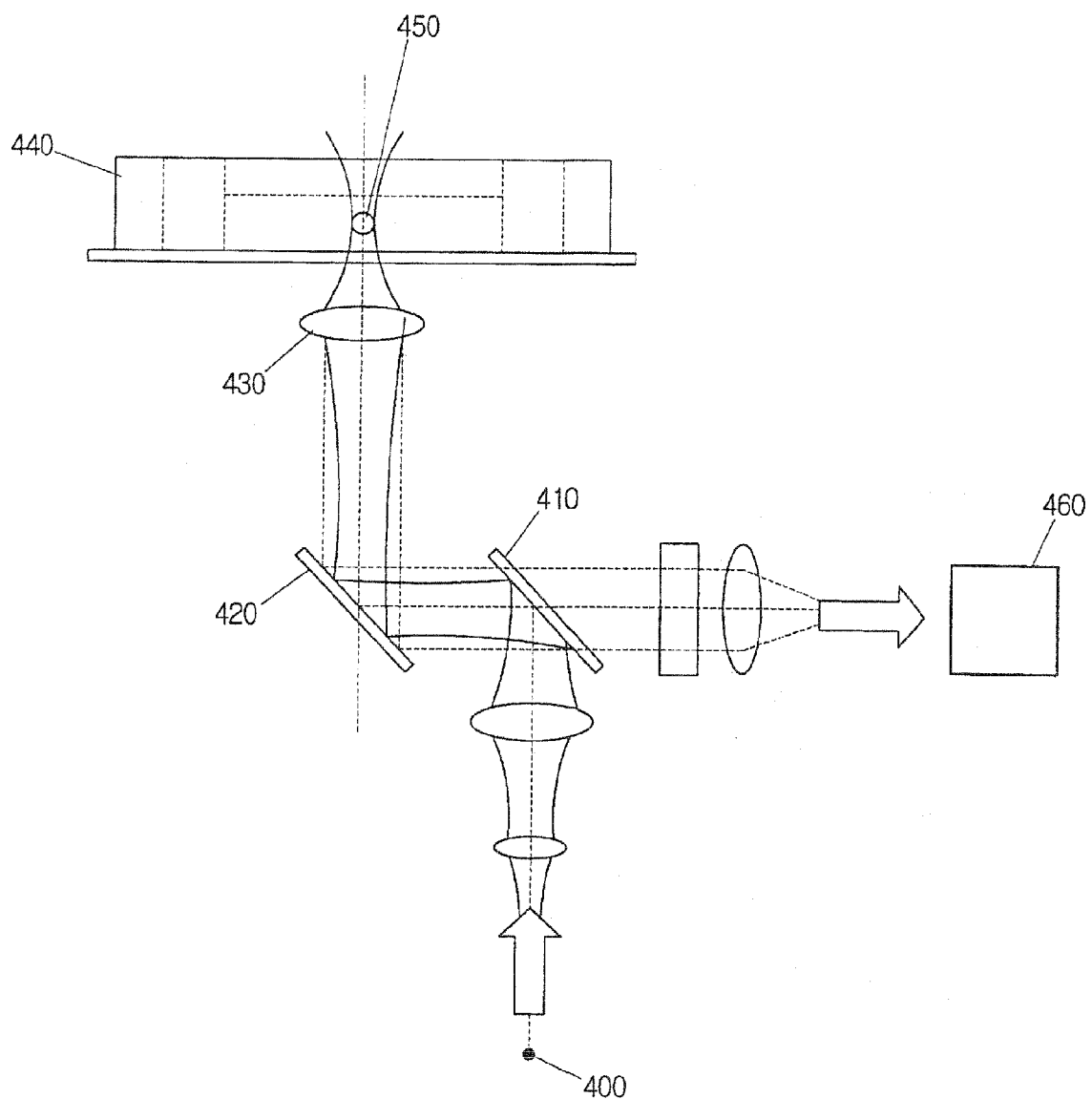
FIG. 4 is a structural view showing another axial illumination device for analyzing micro particles according to the prior art.

DESCRIPTION OF REFERENCE NUMERALS
FOR IMPORTANT PART OF THE DRAWINGS

| | |
|---|---|
| 10, 300, 400, 500: light source | 20, 510: cylindrical lens |
| 30: window | 40, 320, 430: object lens |
| 50, 420, 515: reflecting mirror | 60: aperture |
| 70, 556: filter | |
| 80, 330, 460, 560: signal processing reading section | |
| 90: flow cell | 91: sample injecting inlet |
| 92: buffer solution injecting inlet | 93: observation point |
| 94: buffer solution | 95: sample outlet |
| 310, 410: monochrome mirror | 340: cover slip |
| 440, 540: microchip | 350, 450, 550: micro particles |
| 520: lens having a small numerical aperture | |

-continued

| | |
|---|---|
| 530: concave mirror having a large numerical aperture | |
| 570: hole | 710: microchannel |

BEST MODE FOR CARRYING OUT THE INVENTION

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

Figure 5:
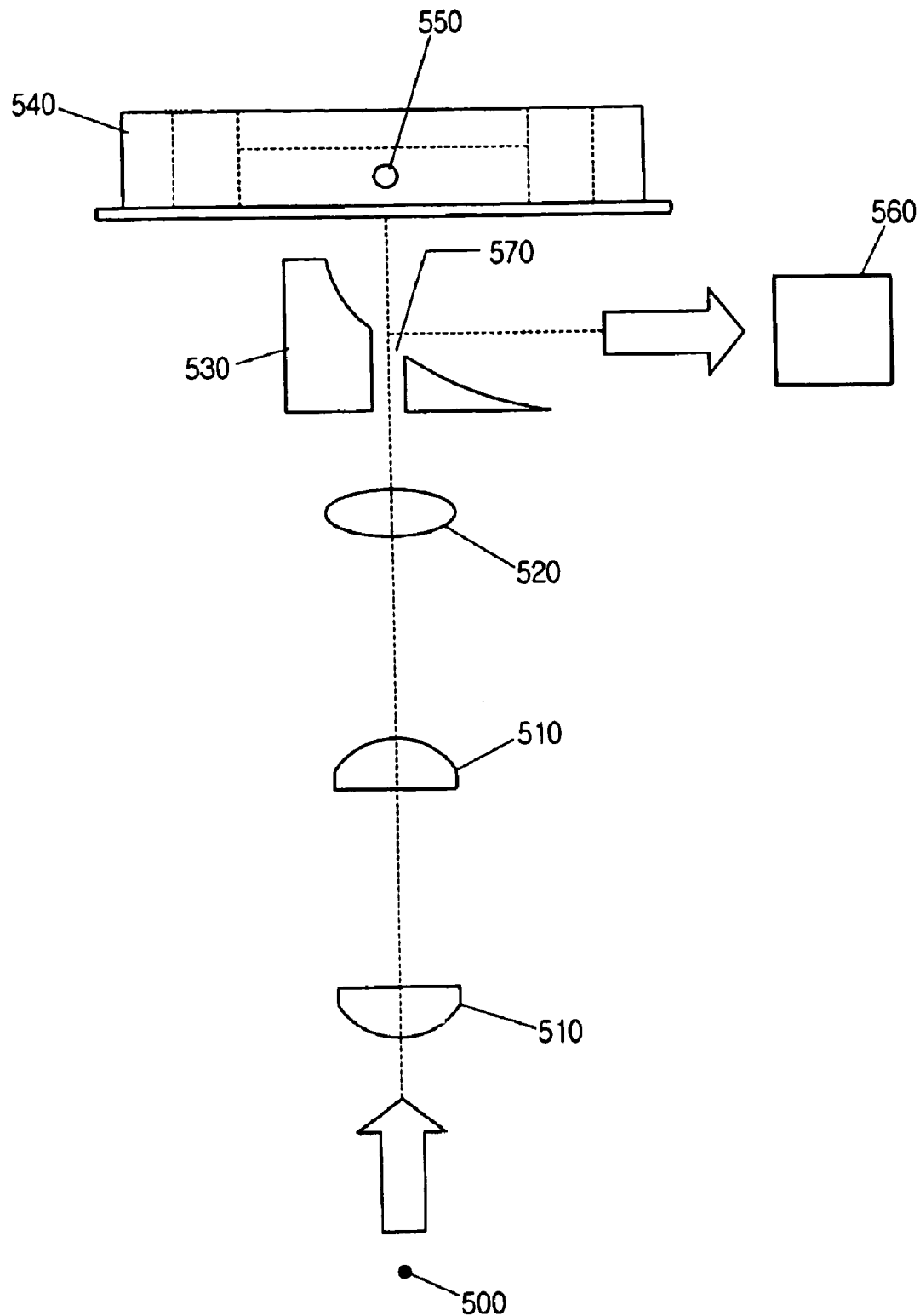
FIG. 5 is a structural view illustrating a micro particle analyzing device according to an embodiment of the invention.
Figure 6:
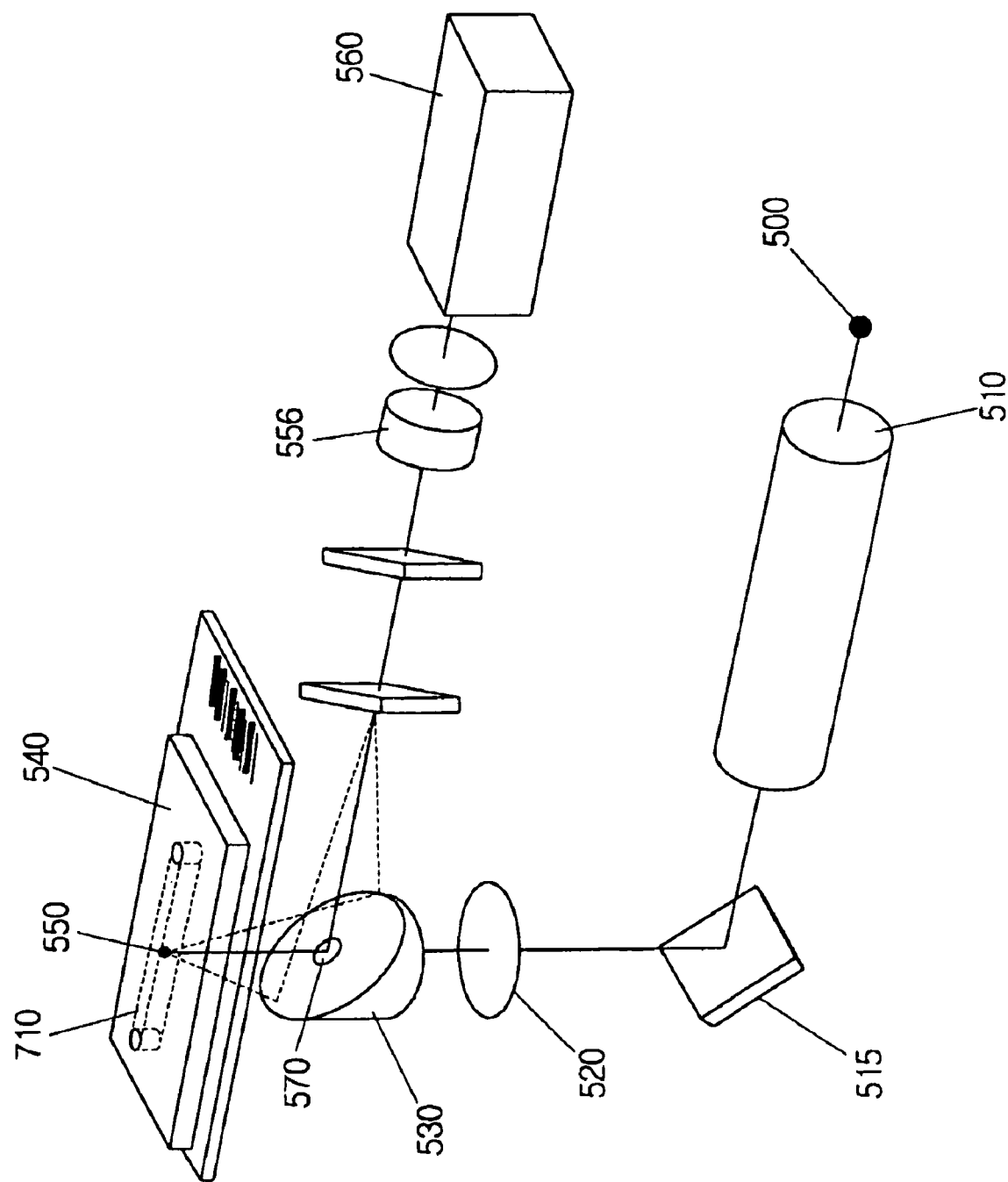
FIG. 6 is a three-dimensional structural view illustrating a micro particle analyzing device according to an embodiment of the invention.

FIG. 5 is a structural view showing a micro particle analyzing device to according to an embodiment of the invention. FIG. 6 three-dimensionally shows a micro particle analyzing device according to an embodiment of the invention.

As shown in FIGS. 5 and 6, the micro particle analyzing device according to an embodiment of the invention illuminates light to fluid comprising a micro particle 550 flowing in a micro channel 710 of a microchip 540, and reads the light emitted from the micro particle at a signal processing reading section 560 to analyze the micro particle.

The micro particle analyzing device comprises a light source section 500 emitting light which will be illuminated to the fluid; a lens 520 regulating an amount of the light emitted from the light source 500 and a focal distance and having a small numerical aperture; and a concave mirror 530 condensing light emitted from the micro particle 550 to reflect it to the reading section 560 and having a large numerical aperture. A hole 570 is formed in the concave mirror 530 so that the light of the light source section 500 having passed through the lens 520 can pass through the concave mirror 530.

The micro particle analyzing device may further comprise a cylindrical lens 510, a reflecting mirror 515, an aperture, and a filter 556, etc.

The light emitted from the light source section 500 passes through the lens 520 having the small numerical aperture, and then is illuminated to the micro particle 550. Since the numerical aperture of the lens 520 is small, a deflection of emission lights according to positions of the micro particles 550 in the micro channel 710 is reduced. After that, the light emitted from the micro particle 550 is condensed by the concave mirror 530 and then transmitted to the reading section 560. Since the numerical aperture of the concave mirror 530 is large, it is possible to condense the light, which is widely emitted, to the maximum extent. In addition, since a diameter of the hole 570 is about 1.5±0.2 mm and very small compared to a magnitude of the concave mirror 530, it is possible to neglect the amount of emission lights which are lost through the hole 570.

Figure 7:
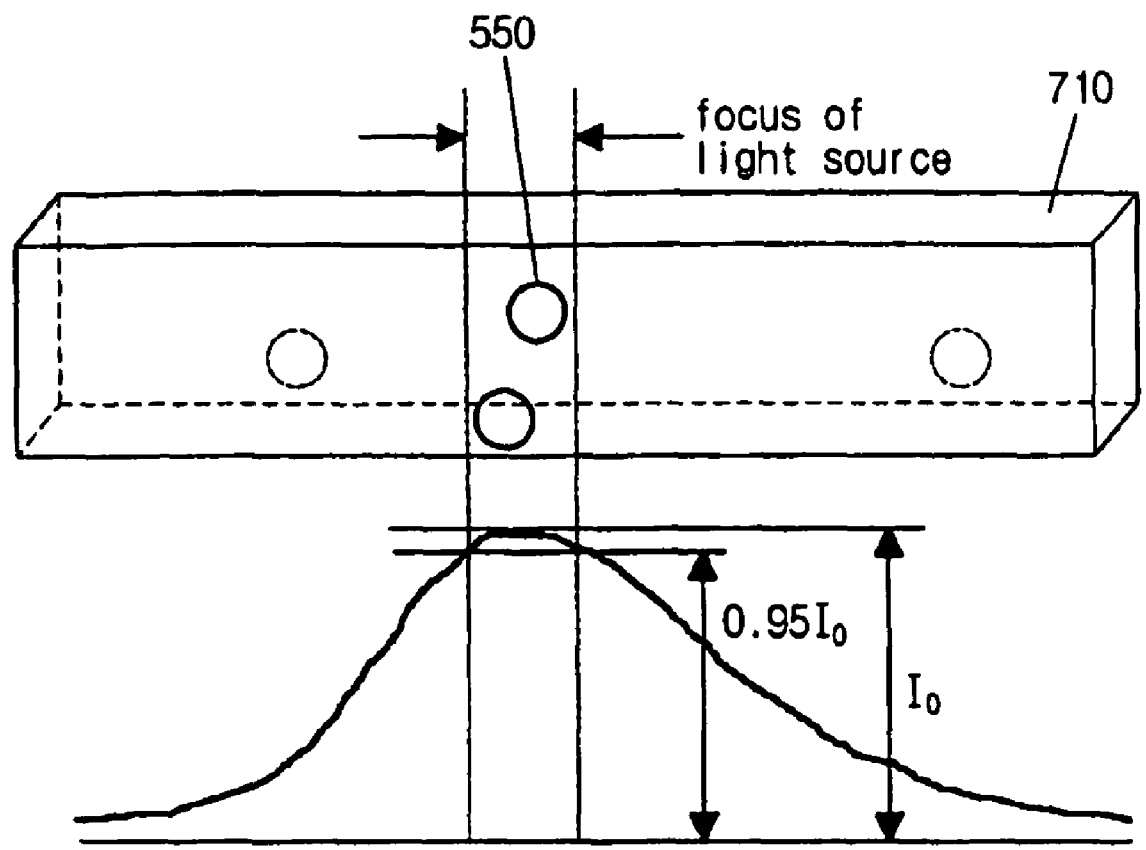
FIG. 7 shows a distribution of magnitudes of lights emitted from micro particles according to positions of the micro particles.

FIG. 7 shows a magnitude distribution of reflected lights according to positions of the micro particle to a focus of a light source. As shown in FIG. 7, when the micro particle is positioned at the focus of the light source, the emission light becomes generally maximal. As the micro particle is farther positioned from the light source, the emission light is reduced.

Figure 8:
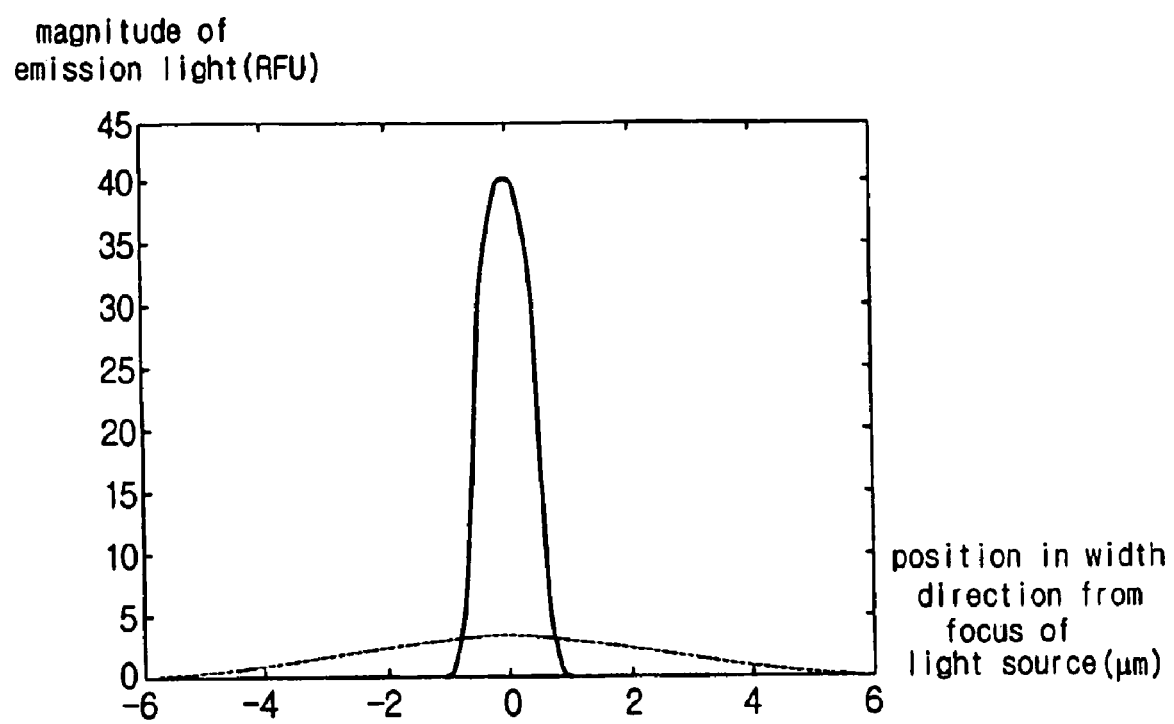
FIGS. 8 to 10 show distributions of emission lights according to positions of micro particles when using an axial illumination device for analyzing micro particles according to the prior art.
Figure 9:
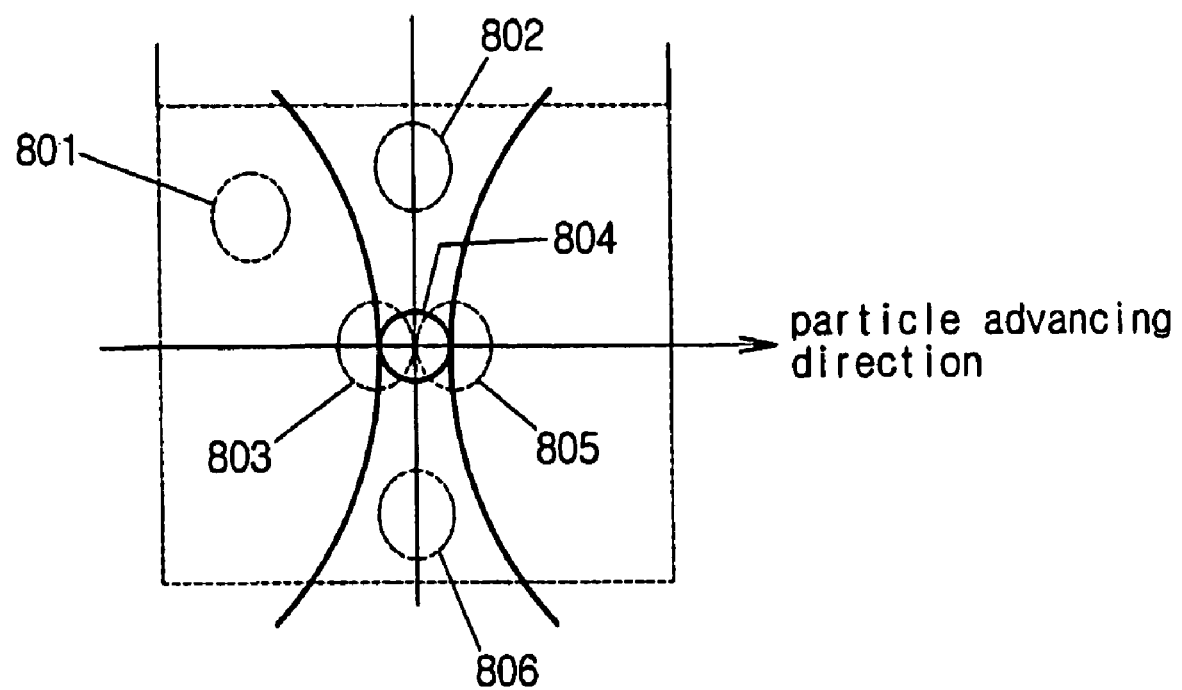
Figure 10:
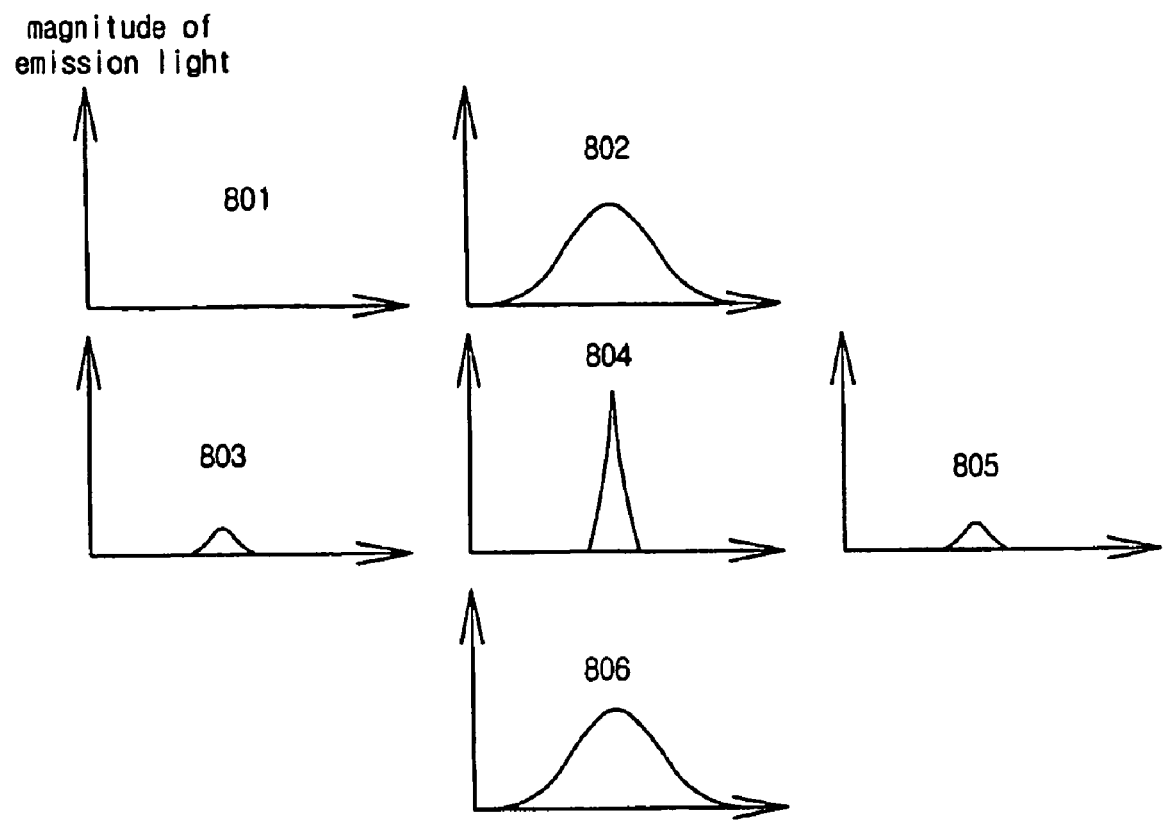

FIGS. 8 to 10 show distributions of emission lights according to positions of the micro particle when using a micro particle analyzing device according to the prior art.

Since the micro particle analyzing device according to the prior art has a limitation on minimizing a numerical aperture of a lens, a lens having a numerical aperture of 0.5 NA was typically used. When using such lens, it can be seen that a magnitude of emission light becomes greatly different according to positions of the micro particle.

FIG. 8 shows a distribution of emission lights according to relative positions of micro particle to a light source. A solid line is a distribution of emission light when the micro particle passes through a middle point for a height direction of the channel. A dotted line is a distribution of emission light when the micro particle flows to a place adjacent to an upper wall surface or lower wall surface. FIG. 10 shows magnitudes of lights emitted from each of the micro particles when the micro particles are detected at places 801 to 806 as shown in FIG. 9.

Since the numerical aperture of incident light is relatively large, the distribution of emission lights is narrow when the micro particle is situated at a middle point for the height direction of the channel. In addition, as shown in FIG. 9, under state that a focus of the light is formed at a center of the channel, it can be seen that the emission light of the micro particle situated above or below the focus is small.

Accordingly, when analyzing the micro particles using the micro particle analyzing device according to the prior art, the focusing should be made so that the micro particles flow at the same height. Accordingly, a correct experimental result can be obtained only when the focusing is made so that the micro particles flow in a row.

Figure 11:
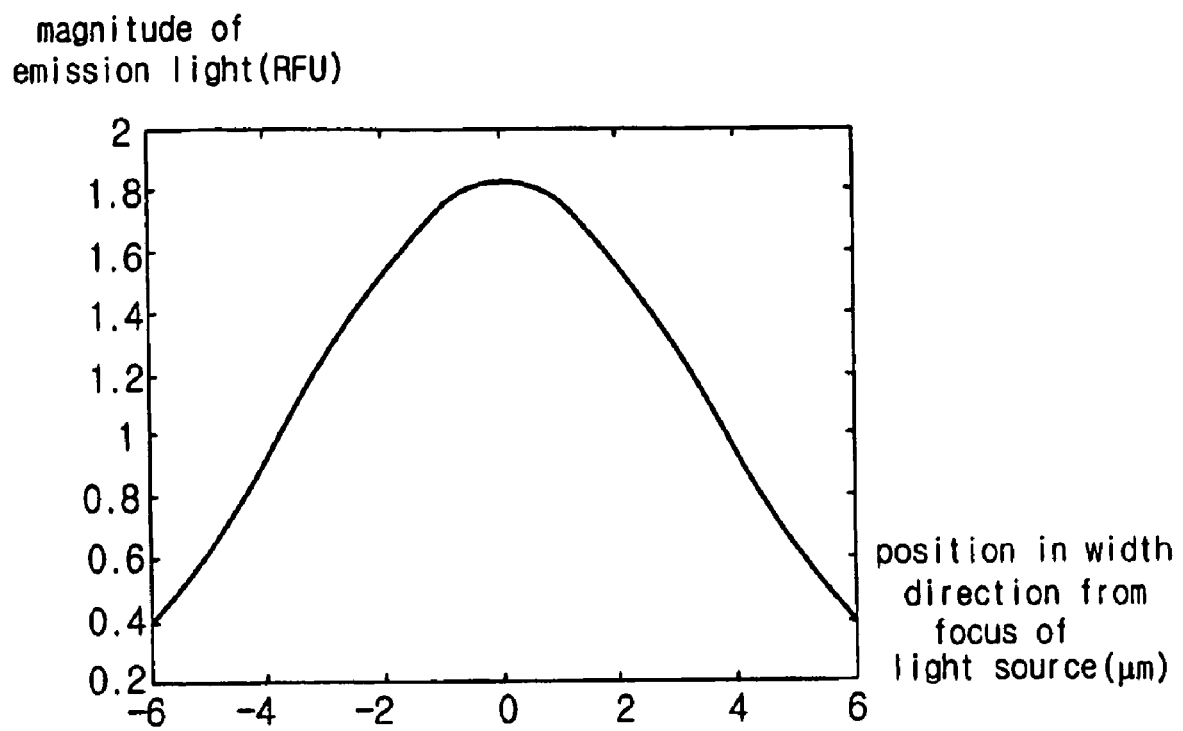
FIGS. 11 to 13 show distributions of emission lights according to positions of micro particles when using a micro particle analyzing device according to an embodiment of the invention.
Figure 12:
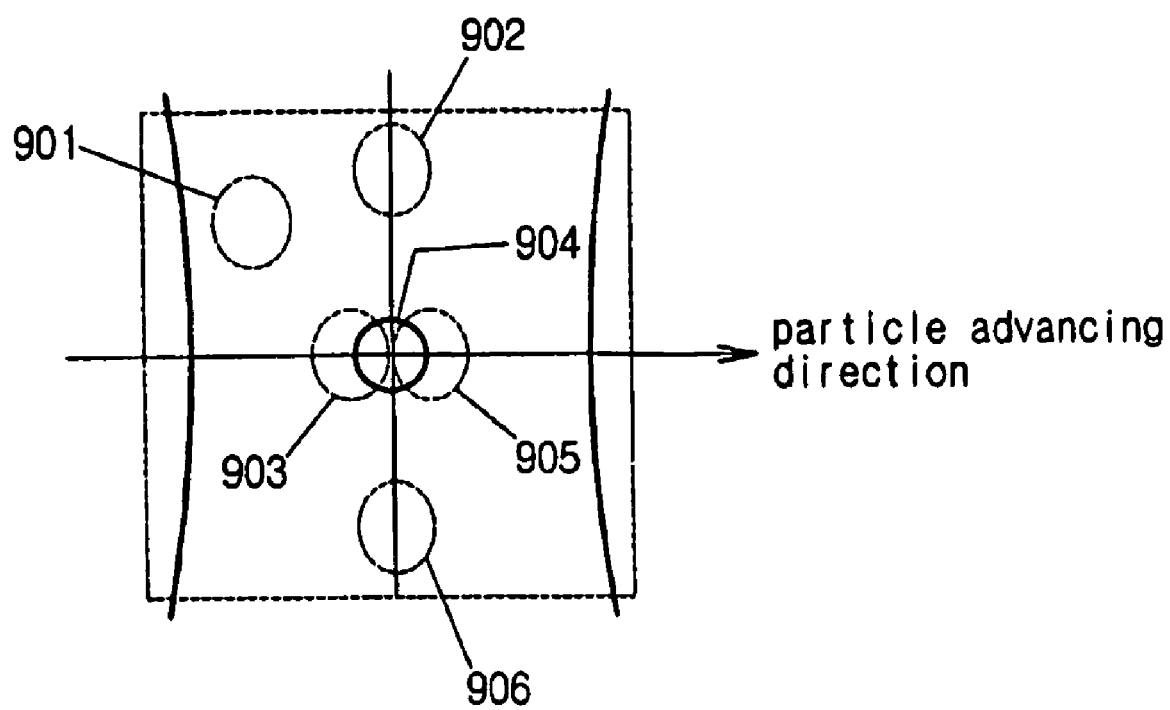
Figure 13:
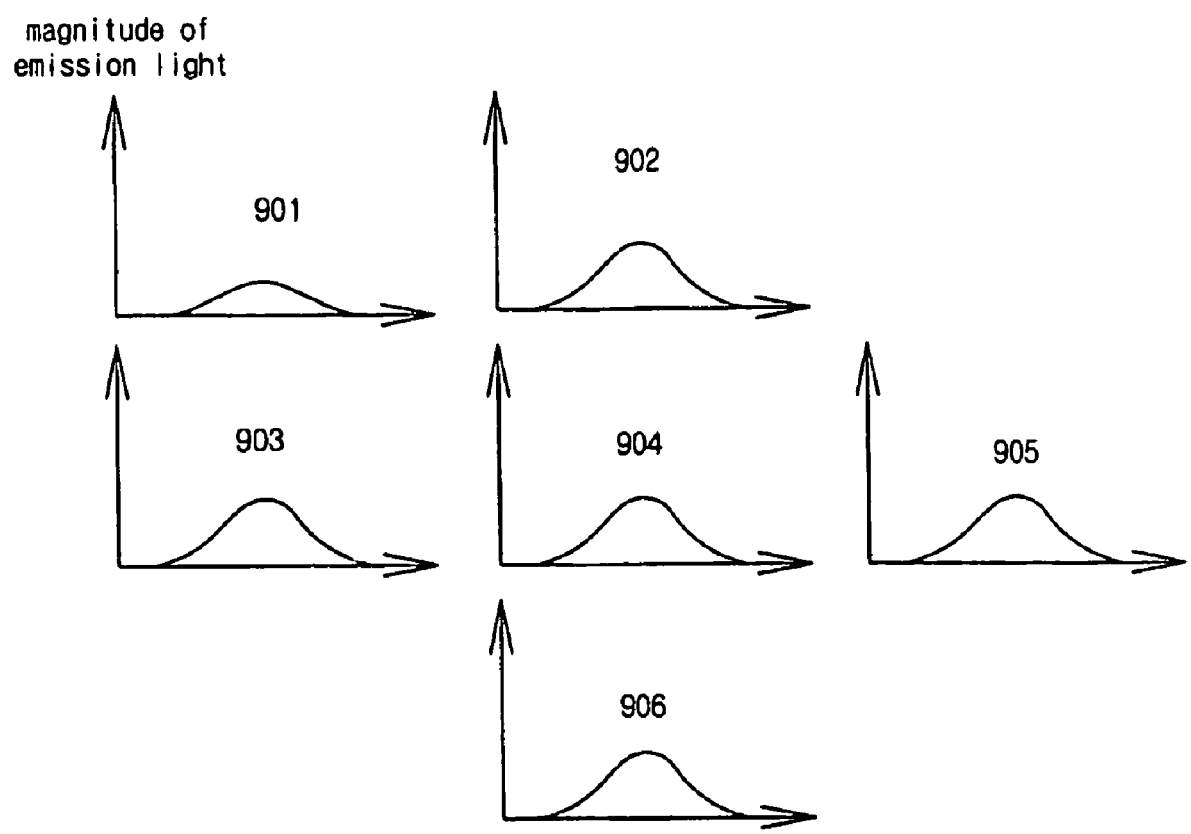

However, the micro particle analyzing device according to the invention can use a lens having a small numerical aperture without any limit. According to the embodiment of the invention, since the lens having 0.01 of numerical aperture is used, a distribution of emission lights according to positions of the micro particles is wider than that of the example shown in FIG. 8, as shown in FIG. 11. Accordingly, magnitudes of the emission lights become not greatly different according to positions of the micro particles. FIG. 13 shows magnitudes of emission lights of each of the micro particles when the micro particles are detected at places 901 to 906 as shown in FIG. 12.

As can be seen from FIG. 13, when compared to the micro particle situated at the focus of the light, the magnitudes of micro particles situated above or below the focus are similar. Accordingly, when using the micro particle analyzing device according to the invention, a correct analysis can be performed even though the focusing is not made so that the micro particles flow in a row. That is, the analysis can be performed without hindrance even when the micro particles flowing in the channel are advanced up and down at the same time.

In addition, it can be seen that the magnitudes of reflected lights, which are situated before and behind the focus of the light, are not greatly changed, too.

FIG. 14 shows examples of real detected signals of micro particles detected at signal processing reading sections of an axial illumination device for analyzing micro particles according to the prior art and a device for analyzing micro particles according to an embodiment of the invention, respectively. As can be seen from FIG. 14, the detected signals are more uniform when using the micro particle analyzing device according to the invention.

Figure 15:
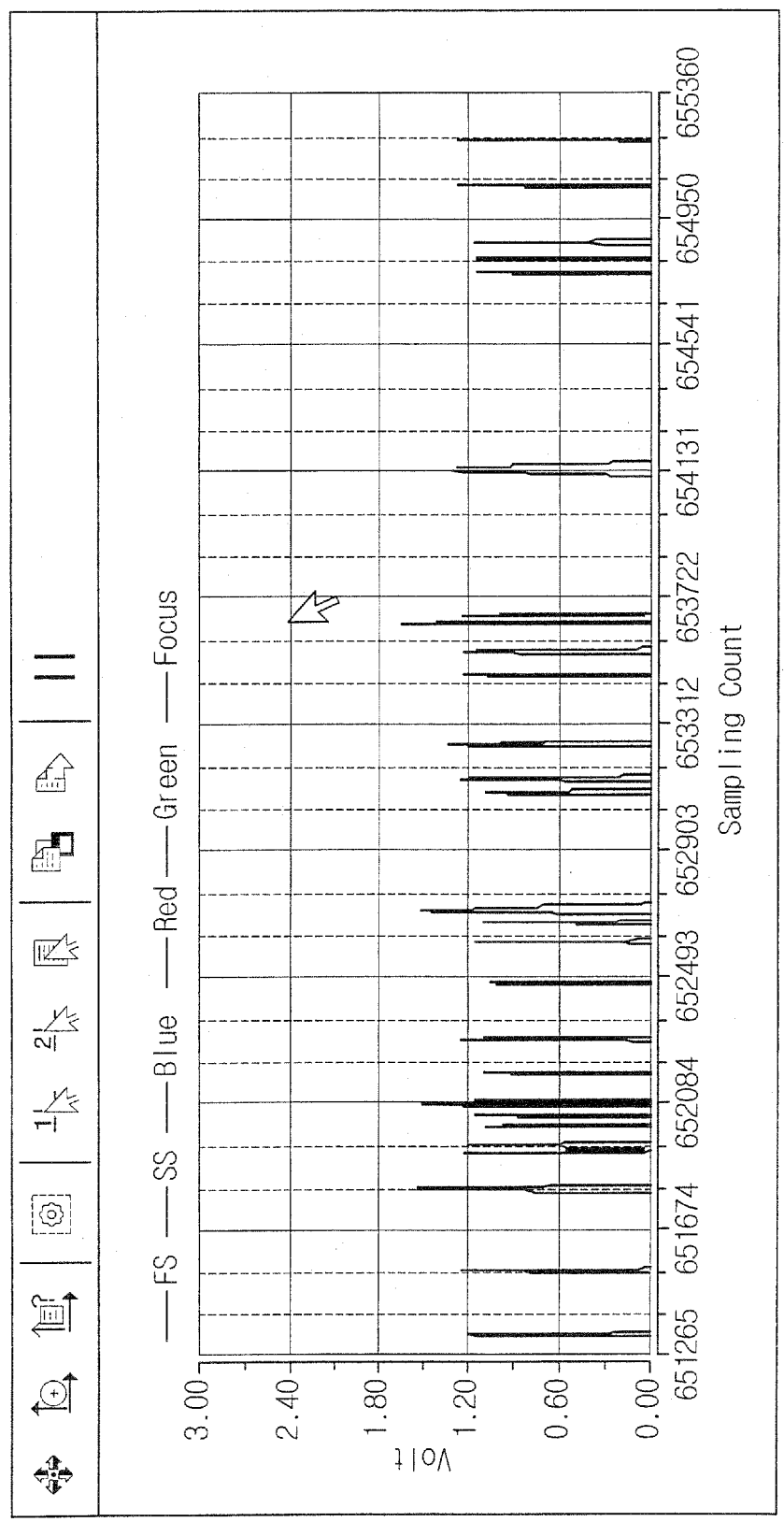
FIG. 15 is a sectional view of a micro channel focusing fluid including micro particles.
Figure 16:
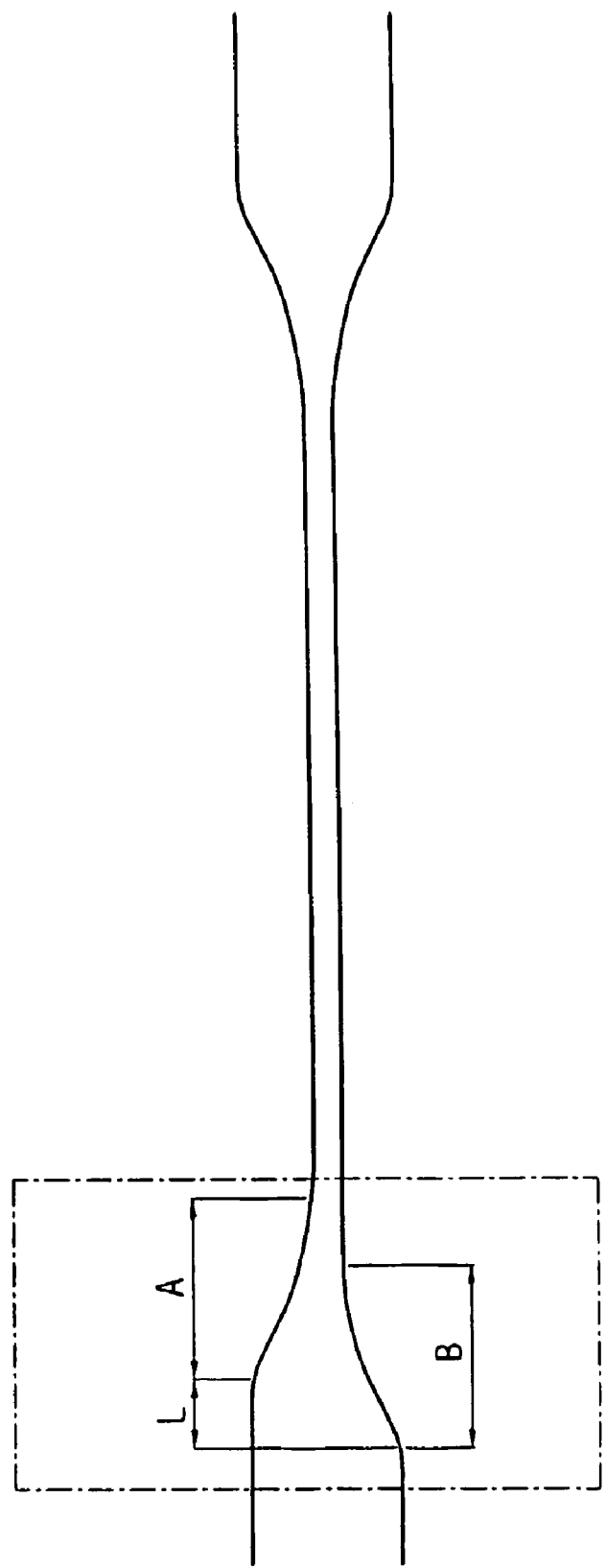

In the mean time, FIG. 15 shows an example of a micro channel having right and left walls asymmetrically formed so that it is possible to prevent the micro particles from combining with each other and thus blocking the channel (i.e., bottleneck phenomenon) when the fluid including the micro particles is focused.

INDUSTRIAL APPLICABILITY

As describe above, when analyzing micro particles using the analyzing device according to the invention, the amounts of lights emitted from the micro particles according to up-and-down positions of the micro particles are not different. Accordingly, it is possible to correctly analyze the micro particles.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A micro particle analyzing device illuminating light to fluid including micro particles, reading a fluorescent light emitted from the micro particles at a signal processing reading section, and thus analyzing the micro particles, comprising:
    a light source section emitting light which will be illuminated to the fluid;
    a lens regulating an amount and a focal distance of the light emitted from the light source; and a concave mirror condensing the fluorescent light emitted from the micro particle to reflect it to the reading section, wherein:
    a hole is formed in the concave mirror so that the light of the light source section having passed through the lens can pass through the concave mirror; the lens is a convex lens and the convex lens is optically combined with the concave mirror; and the numerical aperture of the convex lens is less than 0.1 and the numerical aperture of the concave mirror is 0.1 or more,
        wherein the hole is situated at a place deviated from a central axis of the parabolic mirror,
        wherein a diameter of the hole is about 1 mm~2 mm.

2. The device according to claim 1, wherein the reading section is located at the side of the concave lens, and the concave mirror reflects the fluorescent light in the direction perpendicular to the path of the light illuminated to the fluid so as to reflect the fluorescent light to the reading section.

3. The device according to claim 2, wherein the lens is a convex lens having a small numerical aperture, and the concave mirror has a large numerical aperture.

4. The device according to claim 3, wherein the numerical aperture of the convex lens is 0.1 or less, and the numerical aperture of the concave mirror is 0.1 or more.

5. The device according to claim 2, wherein the concave mirror is a parabolic mirror.

6. The device according to claim 5, wherein the concave mirror is a hemiparabolic mirror.

7. The device according to claim 2, wherein a diameter of the hole is about 1 mm~2 mm.

8. The device according to claim 1, wherein the concave mirror is a parabolic mirror.

9. The device according to claim 8, wherein the concave mirror is a hemiparabolic mirror.

10. The device according to claim 8, wherein the hole is situated at a place deviated from a central axis of the parabolic mirror.

11. A micro particle analyzing device illuminating light to fluid including micro particles, reading a fluorescent light emitted from the micro particles at a signal processing reading section, and thus analyzing the micro particles, comprising:
    a light source section emitting light which will be illuminated to the fluid;
    a lens regulating an amount and a focal distance of the light emitted from the light source; and
    a concave mirror condensing the fluorescent light emitted from the micro particle to reflect it to the reading section, wherein:
        a hole is formed in the concave mirror so that the light of the light source section having passed through the lens can pass through the concave mirror, the reading section is located at the side of the concave lens, and the concave mirror reflects the fluorescent light in the direction perpendicular to the path of the light illuminated to the fluid so as to reflect the fluorescent light to the reading section
        the device illuminates the light to the fluid flowing in a micro channel provided in a microchip made of plastics, the micro channel comprises a nozzle part formed by left and right walls having slanted surfaces so that the fluid is focused to pass through only a predetermined region of the micro channel,
        a cross section of the nozzle part in a width direction is reduced from an inlet of the nozzle part to an outlet of the nozzle part, and
        a longitudinal sectional shape of the micro channel is right and left asymmetrical on the basis of a central line of the micro channel in the longitudinal direction thereof.

12. The device according to claim 11, wherein the slanted surface of any one of the left and right walls constructing the nozzle part is more close to the inlet of the micro channel than the slanted surface of the other wall is.

13. A micro particle analyzing device illuminating light to fluid including micro particles, reading a fluorescent light emitted from the micro particles at a signal processing reading section, and thus analyzing the micro particles, comprising:
    a light source section emitting light which will be illuminated to the fluid;
    a lens regulating an amount and a focal distance of the light emitted from the light source; and
    a concave mirror condensing the fluorescent light emitted from the micro particle to reflect it to the reading section, wherein:
        a hole is formed in the concave mirror so that the light of the light source section having passed through the lens can pass through the concave mirror,
    wherein the device illuminates the light to the fluid flowing in a micro channel provided in a microchip made of plastics,
        the micro channel comprises a nozzle part formed by left and right walls having slanted surfaces so that the fluid is focused to pass through only a predetermined region of the micro channel,
        a cross section of the nozzle part in a width direction is reduced from an inlet of the nozzle part to an outlet of the nozzle part, and
        a longitudinal sectional shape of the micro channel is right and left asymmetrical on the basis of a central line of the micro channel in the longitudinal direction thereof.

14. The device according to claim 13, wherein the slanted surface of any one of the left and right walls constructing the nozzle part is more close to the inlet of the micro channel than the slanted surface of the other wall is.

15. A concave mirror having a large numerical aperture for illuminating light emitted from a light source section to a sample, condensing a fluorescent light emitted from the sample and reflecting it to a signal processing reading section so as to analyze the sample, comprising:

a hole therein so that in optical combination with a lens having a small numerical aperture regulating an amount and a focal distance of the light illuminated to the sample, light of the light source section having passed through the lens can pass through the concave mirror, wherein the lens is a convex lens and the convex lens is optically combined with the concave mirror, the numerical aperture of the convex lens is less than 0.1, and the numerical aperture of the concave mirror is 0.1 or more, wherein the hole is situated at a place deviated from a central axis of the parabolic mirror, wherein a diameter of the hole is about 1 mm~2 mm.

16. The concave mirror according to claim 15, wherein the concave mirror is a hemiparabolic mirror.

* * * * *